US011333637B2

(12) United States Patent
Zhang et al.

(10) Patent No.: US 11,333,637 B2
(45) Date of Patent: May 17, 2022

(54) METHOD FOR DETERMINING CONTENT OF MENTHOL IN PREPARATION OF TRADITIONAL CHINESE MEDICINE COMPOSITION

(71) Applicant: SHIJIAZHUANG YILING PHARMACEUTICAL CO., LTD., Hebei (CN)

(72) Inventors: Shuiying Zhang, Hebei (CN); Dan Bi, Hebei (CN); Yupeng Chen, Hebei (CN); Qian Zhao, Hebei (CN)

(73) Assignee: SHIJIAZHUANG YILING PHARMACEUTICAL CO., LTD., Hebei (CN)

( * ) Notice: Subject to any disclaimer, the term of this patent is extended or adjusted under 35 U.S.C. 154(b) by 474 days.

(21) Appl. No.: 16/347,465

(22) PCT Filed: Nov. 3, 2017

(86) PCT No.: PCT/CN2017/109262
§ 371 (c)(1),
(2) Date: May 3, 2019

(87) PCT Pub. No.: WO2018/082647
PCT Pub. Date: May 11, 2018

(65) Prior Publication Data
US 2021/0285918 A1    Sep. 16, 2021

(30) Foreign Application Priority Data
Nov. 3, 2016 (CN) .......................... 201610949978.1

(51) Int. Cl.
*G01N 30/06* (2006.01)
*G01N 30/30* (2006.01)
(Continued)

(52) U.S. Cl.
CPC ............ *G01N 30/06* (2013.01); *G01N 1/286* (2013.01); *G01N 1/4055* (2013.01);
(Continued)

(58) Field of Classification Search
CPC ........... G01N 2001/2866; G01N 30/54; G01N 2030/3076; G01N 2030/062
See application file for complete search history.

(56) References Cited

FOREIGN PATENT DOCUMENTS

| CN | 101209341 A | 7/2008 |
|---|---|---|
| CN | 101637529 A | 2/2010 |

(Continued)

OTHER PUBLICATIONS

Extended European Search Report, dated May 29, 2020, in European Application No. 17868270.4.
(Continued)

*Primary Examiner* — Paul M. West
(74) *Attorney, Agent, or Firm* — Knobbe, Martens, Olson & Bear LLP

(57) ABSTRACT

A method for determining the content of menthol in a traditional Chinese medicine composition. The traditional Chinese medicine composition consists of the following medicinal materials: *Fructus Forsythia, Flos Lonicerae, Radix Isatidis, Semen Armeniacae Amarum*, menthol, *Herba Houttuyniae*, rheum, *Herba Pogostemonis, Rhizoma Dryopteris Crassirhizomae, Rhodiola rosea* L., *Herba Ephedrae, Radix Glycyrrhizae* and *gypsum*. In the method for determining the content, the content of the menthol in the composition is determined by gas chromatography to effectively control the content of menthol in the composition, and the method can save energy and reduce the costs for analysis.

20 Claims, 2 Drawing Sheets

(51) Int. Cl.
  *G01N 1/28*   (2006.01)
  *G01N 30/54*  (2006.01)
  *G01N 1/40*   (2006.01)
  *G01N 30/34*  (2006.01)
  *G01N 30/60*  (2006.01)
  *G01N 33/15*  (2006.01)
  *G01N 30/02*  (2006.01)

(52) U.S. Cl.
  CPC ........... *G01N 1/4077* (2013.01); *G01N 30/30* (2013.01); *G01N 30/34* (2013.01); *G01N 30/54* (2013.01); *G01N 30/6078* (2013.01); *G01N 33/15* (2013.01); *G01N 2001/2866* (2013.01); *G01N 2001/4061* (2013.01); *G01N 2001/4088* (2013.01); *G01N 2030/025* (2013.01); *G01N 2030/062* (2013.01); *G01N 2030/3076* (2013.01)

(56) References Cited

FOREIGN PATENT DOCUMENTS

| | | | |
|---|---|---|---|
| CN | 101 744 946 A | | 6/2010 |
| CN | 101744946 A | | 6/2010 |
| CN | 101991785 A | | 3/2011 |
| CN | 102058829 A | | 5/2011 |
| CN | 102120005 A | | 7/2011 |
| CN | 103 800 523 A | | 5/2014 |
| CN | 104345111 A | | 2/2015 |
| CN | 104792895 A | | 7/2015 |
| CN | 104 950 052 A | | 9/2015 |
| CN | 105 717 214 A | | 6/2016 |
| CN | 105717214 A | | 6/2016 |
| CN | 104950052 B | * | 2/2018 |
| JP | 2004-301775 A | | 10/2004 |
| JP | 2004301775 A | | 10/2004 |
| JP | 4088776 B2 | | 5/2008 |

OTHER PUBLICATIONS

Qiao, J., et al., Contents Determination of Menthol in Lianhuaqingwen Capsule by Gas Chromatography, Journal of Hubei University of Medicine, vol. 32, No. 6, pp. 470-472, 2013.
International Search Report and Written Opinion, dated Jan. 29, 2018, in International Application No. PCT/CN2017/109262.
Office Action dated Aug. 11, 2020 in Canadian Application No. 3042612.
Mesaros, C., et al., "GC-MS Characterization of the Compounds in Some Essential Oils", Bulletin UASVM Agriculture, vol. 66, pp. 1843-5386 (2010).
Nicolli et al., "Characterization of the Volatile Profile of Brazilian Moscatel Sparkling Wines Through Solid Phase Microextraction and Gas Chromatography", J. Braz. Chem. Soc., vol. 26, No. 7, pp. 1411-1430 (Jul. 2015).
Chickos et al., "An Examination of Factors Influencing the Thermodynamics of Correlation-Gas Chromatography as Applied to Large Molecules and Chiral Separations", Journal of Chemical & Engineering Data, vol. 55, No. 2, pp. 698-707 (2010).
Notice of Preliminary Rejection dated Jul. 20, 2020 in Korean Application No. 10-2019-7015749.
International Preliminary Report On Patentability dated May 7, 2019 in International Application No. PCT/CN2017/109262.
Written Opinion dated Jan. 29, 2018 in International Application No. PCT/CN2017/109262.
Office Action dated Jun. 24, 2021 in Chinese Patent Application No. 201610949978.1.
Xu et al., GC determination of menthol and Borneol in Shezhi Bingfu Ointment, Chinese Journal of Pharmaceutical Analysis, vol. 31, No. 11, pp. 2158-2160, 2011.
Zhang et al., Determination of menthol, guaiacol and eugenol in Dutong Jianwei Zhengchang Pills by GC, Chinese Traditional Patent Medicine, vol. 35, No. 2, pp. 286-289, 2013.
Zhang et al., Quantitative Determination of Borneol in Qiangxin Dripping Pills by Capillary Gas Chromatography, Chemical Industry and Engineering, vol. 24, No. 3, pp. 215-217, 2007.

* cited by examiner

METHOD FOR DETERMINING CONTENT OF MENTHOL IN PREPARATION OF TRADITIONAL CHINESE MEDICINE COMPOSITION

PRIORITY AND CROSS REFERENCE TO RELATED APPLICATIONS

This application is the U.S. National Stage Application under 35 U.S.C. § 371 of International Application No. PCT/CN2017/109262, filed Nov. 3, 2017, designating the U.S. and published as WO 2018/082647 A1 on May 11, 2018, which claims the benefit of Chinese Patent Application No. CN 201610949978.1, filed Nov. 3, 2016. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a method for determining the content of menthol in a preparation of a traditional Chinese medicine composition.

TECHNICAL BACKGROUND

Gas chromatography is to vaporize the analytical sample in the inlet, then carry the vaporized sample by a carrier gas into a chromatographic column, and the components of the sample are separated by a chromatographic column with different retention properties for the components of the mixture to be tested and then are sequentially introduced into detectors to obtain detection signals for the components. According to the order of introducing the components into the detectors, upon comparison, it is possible to identify peaks of the components, and the content of each component can be calculated according to the peak height or the peak area.

Menthol is extracted from the leaves and stems of mint, a white crystal, and the main ingredient of mint and peppermint essential oils. In the world, India is the main producer of natural mint. Both menthol and racemic menthol can be used as flavoring agents for toothpastes, perfumes, beverages and candies. Menthol is used as a stimulant in medicine, it is applied on skins or mucous membranes and has cooling and antipruritic effects. Orally administered menthol can be used as a medicine for dispelling rheumatic pains and colds, etc., which are used for headache and inflammations of the nose, pharynx and throat. Menthol esters are used in spices and medicines. At present, gas chromatography is widely used in the quality control of traditional Chinese medicines, especially in the detection of volatile components. The quality control and evaluation of compound traditional Chinese medicines is one of the key issues in the modernization of traditional Chinese medicines and also a difficulty and focus in the research of traditional Chinese medicines, especially the control of volatile chemical components. The purpose of quality control of traditional Chinese medicines is to ensure the effectiveness and safety of traditional Chinese medicines. The quality control of traditional Chinese medicines is to monitor the pharmacodynamic substances, toxic substances of traditional Chinese medicines as well as changing rules thereof, and to conduct quality examination and control on each section of the process for producing traditional Chinese medicines based on a series of quality standards. Moreover, research on the techniques, methods and strategies for the quality evaluation of traditional Chinese medicines is the basis for making scientific, rational and advanced quality standards.

The present invention seeks to protect a method for determining the content of menthol in a traditional Chinese medicine composition, which is composed of the following medicinal materials: *Fructus Forsythia, Flos Lonicerae, Radix Isatidis, Semen Armeniacae Amarum*, menthol, *Herba Houttuyniae*, rheum, *Herba Pogostemonis, Rhizoma Dryopteris Crassirhizomae, Rhodiola rosea* L., *Herba Ephedrae, Radix Glycyrrhizae* and *gypsum*. In the determination method, the content of menthol in the composition is determined by gas chromatography to effectively control the content of menthol in the composition. The method can save energy and reduce the costs for analysis and it is not disclosed in the prior art.

SUMMARY

The present invention provides a method for determining the content of menthol in a preparation of a traditional Chinese medicine composition, which is prepared from the following raw materials by weight: *Fructus Forsythia* 200-300, *Herba Ephedrae* 60-100, rheum 40-60, *Herba Houttuyniae* 200-300, *Flos Lonicerae* 200-300, *Radix Isatidis* 200-300, *Herba Pogostemonis* 60-100, *Rhizoma Dryopteris Crassirhizomae* 200-300, *Rhodiola rosea* L. 60-100, menthol 5-9, *Semen Armeniacae Amarum* 60-100, *Radix Glycyrrhizae* 60-100 and *gypsum* 200-300, wherein the content of the menthol is determined according to the method as follows:

1) extracting the preparation of the traditional Chinese medicine composition using a non-polar solvent to obtain a test solution;

2) preparing a solution of menthol reference substance with a menthol concentration of 4.80 µg/mL or more, preferably 17.65 µg/mL or more, more preferably 0.2-0.3 mg/mL by a menthol reference substance using the same non-polar solvent as in step 1);

3) taking the solution of menthol reference substance and the test solution in an equal amount respectively, injecting the solutions into a gas chromatograph, and determining the contents of menthol, wherein the conditions for chromatography are:

the column is a weak polar capillary chromatographic column; the column temperature is increased according to the following temperature programming: initial temperature 80-100° C., the initial temperature is kept for 10-15 minutes and increased to 120-160° C. at a rate of 6-10° C. per minute, kept for 1.5-3.5 minutes, then increased to 240-300° C. at a rate of 100-160° C. per minute, kept for 5-20 minutes.

In some embodiments of the present invention, the mass-to-volume ratio of the preparation of the traditional Chinese medicine composition to the non-polar solvent as used is (1 g:400 mL) to (1 g:50 mL) during the preparation of the test solution.

In some embodiments of the present invention, the weak polar capillary chromatographic column contains phenyl-methyl polysiloxane as a stationary phase, and preferably the phenyl-methyl polysiloxane has a phenyl content of 1-10%, more preferably 5%, i.e., a capillary chromatographic column having a 5% phenyl-95% methyl polysiloxane as a stationary phase. Particularly preferably, a capillary chromatographic column of type HP-5 or DB-5 is used in the present invention.

In some embodiments of the present invention, the solution of menthol reference substance and the test solution are injected in an amount of 0.5-2 μL, respectively, and may be injected in an amount of 0.5 μL, 1 μL, 1.5 μL or 2 μL, etc.

In some embodiments of the present invention, in the chromatographic test, the solution of menthol reference substance and the test solution are injected by split injection with a split ratio in the range of 50:1 to 10:1, preferably 30:1 to 20:1, for example, 25:1.

In some embodiments of the present invention, a fuel gas ratio is also included in the conditions for chromatography. It is generally known to those skilled in the art that the amount and ratio of fuel gases used in gas chromatography are related to the detector used in the chromatograph. In some embodiments of the present invention, the fuel gas ratio is the ratio of air to hydrogen being from 8:1 to 12:1, preferably from 9:1 to 11:1, most preferably 10:1.

In some embodiments of the present invention, the conditions for chromatography further comprise a detector temperature and an inlet temperature, which are 300-400° C., respectively. In some embodiments of the present invention, the conditions for chromatography further comprise a carrier gas and a flow rate thereof, the carrier gas is nitrogen, at a flow rate of 0.8-1.2 mL/min.

In some embodiments of the present invention, the non-polar solvent used to dissolve the solution of the menthol reference substance and the test article is selected from the group consisting of non-polar saturated alkanes or halogenated saturated alkanes, and non-polar ester solvents, particularly n-hexane, dichloromethane, petroleum ether and ethyl acetate, preferably n-hexane.

In some embodiments of the present invention, the method for preparing the test solution specifically is as follows: grinding and mixing a certain amount of the preparation of the traditional Chinese medicine composition evenly, placing the obtained substance in a narrow mouth container equipped with a plug, adding the non-polar organic solvent, shaking for 20 seconds or more, filtering then obtaining the test solution. In some preferred embodiments, the filtering step is carried out using a 0.2-0.4 μm microporous filter, preferably using a 0.22 μm microporous filter. In some preferred embodiments, the method for preparing the test solution further comprises the step of soaking or ultrasonical extraction at room temperature before the shaking step.

The solution of menthol reference substance of the present invention can be prepared using methods conventionally used in the art. A preferable way is to take appropriate amount of menthol reference substance and weigh accurately, and add non-polar organic solvent to prepare a solution of menthol reference substance with a concentration of 4.80 μg/mL or more, preferably 17.65 μg/mL or more, more preferably 0.2-0.3 mg/mL, especially 0.23 mg/mL.

In an embodiment of the present invention, the substance contained in the Lianhua Qingwen preparation (such as tablets or granules) that is already on the market can be used directly in the preparation of the traditional Chinese medicine composition to be tested, the preparation of the traditional Chinese medicine composition to be tested can also be prepared by the following method:

(1) weighing traditional Chinese medicines according to the weight ratio of raw materials, selecting the medicinal parts and processing into pieces; (2) adding water to *Herba Pogostemonis* to extract volatile oil (the ratio of the volume of water to the weight of medicinal material (L/kg, mL/g) is 8-12) to extract volatile oil, oil extraction time is 6-10 hours, collecting the volatile oil for later use; after the extract is filtered, keeping the filtrate for later use;

(3) extracting *Fructus Forsythia, Herba Ephedrae, Herba Houttuyniae* and *rheum* with 60%-80% (v/v) ethanol (the ratio of the volume of ethanol to the weight of medicinal materials (L/kg, mL/g) is 10-14) for 2-4 times, each time of extraction takes 1.5-3 hours, combining the extracts and filtering, keeping the filtrate for later use;

(4) adding water to *Flos Lonicerae, gypsum, Radix Isatidis, Rhizoma Dryopteris Crassirhizomae, Radix Glycyrrhizae* and *Rhodiola rosea* L. (the ratio of the volume of the water to the weight of the medicinal materials (L/kg, mL/g) is 10-14) and decocting the obtained mixture until the mixture is boiled, adding *Semen Armeniacae Amarum*, decocting the obtained mixture for 2-4 times with each decoction of 0.5-2 hours, combining and filtering the extracts, combining the obtained filtrate with the filtrate obtained after the oil extraction of *Herba Pogostemonis* in step (2), concentrating the obtained combination to obtain a clear paste with a relative density of 1.10-1.15 determined at 50-70° C., adding ethanol, adjusting to an alcohol concentration of 65-80%, refrigerating and filtering until the filter residue has no smell of alcohol, obtaining a clear paste for later use;

(5) combining the clear paste obtained in step (4) with the ethanol extract in step (3), concentrating to obtain a clear paste with a relative density of 1.15-1.20 determined at 50-70° C., drying to obtain dry paste powders for later use;

(6) adding the dry paste powders obtained in step (5) to a suitable pharmaceutically acceptable auxiliary material for granulation;

(7) adding menthol and the volatile oil obtained in step (2) to ethanol and allowing the menthol and volatile oil dissolved in ethanol, and spraying the granules obtained in step (6) into the obtained mixture, sealing, mixing evenly, tabletting or encapsulating or bagging.

In some embodiments of the present invention, the pharmaceutically acceptable auxiliary material is starch.

In some embodiments of the present invention, a method for determining the content of menthol in a traditional Chinese medicine composition is provided. The traditional Chinese medicine composition is prepared from the following raw materials by weight: *Fructus Forsythia* 200-300, *Herba Ephedrae* 60-100, rheum 40-60, *Herba Houttuyniae* 200-300, *Flos Lonicerae* 200-300, *Radix Isatidis* 200-300, *Herba Pogostemonis* 60-100, *Rhizoma Dryopteris Crassirhizomae* 200-300, *Rhodiola rosea* L. 60-100, menthol 5-9, *Semen Armeniacae Amarum* 60-100, *Radix Glycyrrhizae* 60-100 and *gypsum* 200-300, the method for determining the content of the menthol is as follows:

test solution preparation: taking the substance contained in the composition from the samples of loading difference test, grinding finely, mixing evenly, taking 0.2-0.5 g, accurately weighing, placing in a conical flask equipped with a plug, adding 20-30 mL of n-hexane accurately, shaking the flask clockwise and counterclockwise for about 20-50 seconds, taking a suitable amount of solution, filtering through a 0.22 μm microporous membrane to obtain the test solution;

preparation of the solution of reference substance: taking a suitable amount of menthol reference substance, weighing accurately, adding n-hexane to prepare a menthol solution with a menthol concentration of 0.23 mg per 1 mL of n-hexane to obtain the solution of menthol reference substance;

conditions for chromatography: chromatographic column: Agilent J&W Scientific HP-5 capillary chromatographic column (30 m×0.25 mm, 0.25 μm); the column temperature is increased according to the following temperature programming: initial temperature 98° C., the temperature is kept for 12 minutes, increased to 140° C. at a rate of 8° C. per minute, kept for 2.5 minutes, then increased to 280° C. at a rate of 140° C. per minute, kept for 5-20 minutes; detector temperature is 300-400° C.; inlet temperature is 300-400° C.; carrier gas is nitrogen, flow rate: 0.8-1.2 mL/min; injection by split injection, split ratio: 25:1; the volume of injected sample: 0.5-2 μL; fuel gas ratio: air-hydrogen (450:45);

determination method: accurately taking 0.5-2 μL of the solution of menthol and 0.5-2 μL of the test solution, respectively, injecting the taken solution into a gas chromatograph for determining.

In some embodiments of the present invention, the preparation of the traditional Chinese medicine composition of the present invention is prepared from the following raw material by weight:

Fructus Forsythia 200, Flos Lonicerae 300, Radix Isatidis 200, rheum 40, Herba Pogostemonis 60, Rhizoma Dryopteris Crassirhizomae 300, Rhodiola rosea L. 100, menthol 9, Herba Ephedrae 60, Semen Armeniacae Amarum 100, Herba Houttuyniae 200, Radix Glycyrrhizae 100 and gypsum 200.

In some embodiments of the present invention, preferred parts by weight of the preparation of the traditional Chinese medicine composition of the invention are as follows:

Fructus Forsythia 300, Flos Lonicerae 200, Radix Isatidis 300, rheum 60, Herba Pogostemonis 100, Rhizoma Dryopteris Crassirhizomae 200, Rhodiola rosea L. 60, menthol 5, Herba Ephedrae 100, Semen Armeniacae Amarum 60, Herba Houttuyniae 300, Radix Glycyrrhizae 60 and gypsum 300.

In some embodiments of the present invention, preferred parts by weight of the preparation of the traditional Chinese medicine composition of the invention are as follows:

Fructus Forsythia 278, Flos Lonicerae 294, Radix Isatidis 285, rheum 55, Herba Pogostemonis 95, Rhizoma Dryopteris Crassirhizomae 290, Rhodiola rosea L. 87, menthol 8.5, Herba Ephedrae 88, Semen Armeniacae Amarum 80, Herba Houttuyniae 284, Radix Glycyrrhizae 95 and gypsum 277.

In some embodiments of the present invention, preferred parts by weight of the preparation of the traditional Chinese medicine composition of the invention are as follows:

Fructus Forsythia 255, Flos Lonicerae 255, Radix Isatidis 255, rheum 51, Herba Pogostemonis 85, Rhizoma Dryopteris Crassirhizomae 255, Rhodiola rosea L. 85, menthol 7.5, Herba Ephedrae 85, Semen Armeniacae Amarum 85, Herba Houttuyniae 255, Radix Glycyrrhizae 85 and gypsum 255.

In some embodiments of the present invention, the method for preparing of the traditional Chinese medicine composition of the present invention is as follows:

(1) weighing traditional Chinese medicines according to the weight ratio of raw materials, selecting the medicinal parts and processing into pieces as required;

(2) processing Herba Pogostemonis into pieces, adding water (the ratio of the volume of water to the weight of medicinal material (L/kg, mL/g) is 10) to extract volatile oil, oil extraction time is 8 hours, collecting the volatile oil for later use; after the extract is filtered, removing the residue, keeping the filtrate for later use;

(3) extracting Fructus Forsythia, Herba Ephedrae, Herba Houttuyniae and rheum with 70% (v/v) ethanol (the ratio of the volume of water to the weight of medicinal material (L/kg, mL/g) is 12) for 3 times and each time of extraction takes 2.5 hours, combining the extracts and filtering, recycling the ethanol, keeping the filtrate for later use;

(4) adding water to Flos Lonicerae, gypsum, Radix Isatidis, Rhizoma Dryopteris Crassirhizomae, Radix Glycyrrhizae and Rhodiola rosea L. (the ratio of the volume of the water to the weight of the medicinal material (L/kg, mL/g) is 12) and decocting the obtained mixture until the mixture is boiled, adding Semen Armeniacae Amarum, decocting the obtained mixture for 2 times and each deoction takes 1 hour, combining and filtering the extracts, combining the obtained filtrate with the filtrate obtained after the oil extraction of Herba Pogostemonis in step (2), concentrating the obtained combination to obtain a clear paste with a relative density of 1.10-1.15 determined at 60° C., adding ethanol, adjusting to an alcohol concentration of 70%, refrigerating, filtering, recycling the ethanol until there's no smell of alcohol, obtaining a clear paste for later use;

(5) combining the clear paste obtained in step (4) with the ethanol extract in step (3), concentrating to obtain a clear paste with a relative density of 1.15-1.20 determined at 60° C., drying to obtain dry paste powders for later use;

(6) adding the dry paste powders obtained in step (5) to a suitable pharmaceutically acceptable auxiliary material for granulation;

(7) adding menthol and the volatile oil obtained in step (2) to ethanol and allowing the menthol and volatile oil dissolved in ethanol, and spraying the granules obtained in step (6) into the obtained mixture, sealing, mixing evenly, tabletting or encapsulating or bagging.

In some embodiments of the present invention, the method for determining the content of menthol in a traditional Chinese medicine composition is.

test solution preparation: taking the substance contained in the composition from the samples of loading difference test, grinding finely, mixing evenly, taking 0.3 g, accurately weighing, placing in a conical flask equipped with a plug, adding 25 mL of n-hexane accurately, shaking the flask clockwise and counterclockwise for about 30 seconds, taking a suitable amount of solution, filtering through a 0.22 μm microporous membrane to obtain the test solution;

preparation of the solution of reference substance: taking a suitable amount of menthol reference substance, weighing accurately, adding n-hexane to prepare a menthol solution with a menthol concentration of 0.23 mg per 1 mL to obtain the solution of menthol reference substance;

conditions for chromatography: chromatographic column: Agilent J&W Scientific HP-5 capillary chromatographic column (30 m×0.25 mm, 0.25 μm); the column temperature is increased according to the following temperature programming: initial temperature is 98° C., the temperature is kept for 12 minutes, increased to 140° C. at a rate of 8° C. per minute, kept for 2.5 minutes, then increased to 280° C. at a rate of 140° C. per minute, kept for 10 minutes; detector temperature is 300° C.; inlet temperature is 300° C.; carrier gas is nitrogen, flow rate: 1 mL/min; injection by split injection, split ratio: 25:1; the volume of injected sample: 1 μL; fuel gas ratio: air-hydrogen (450:45);

determination method: accurately taking 1 μL of the solution of menthol reference substance and 1 μL of the test solution, respectively, injecting the solutions into a gas chromatograph, determining then obtaining the results.

Optionally, the method for determining the content of the present invention is as follows:

test solution preparation: taking the substance contained in the composition from the samples of loading difference test, grinding finely, mixing evenly, taking 0.2 g, accurately weighing, placing in a conical flask equipped with a plug, adding 20 mL of n-hexane accurately, shaking the flask clockwise and counterclockwise for about 20 seconds, taking a suitable amount of solution, filtering through a 0.22 μm microporous membrane to obtain the test solution;

preparation of the solution of reference substance: taking a suitable amount of menthol reference substance, weighing accurately, adding n-hexane to prepare a menthol solution with a menthol concentration of 0.23 mg per 1 mL of n-hexane to obtain the solution of menthol reference substance;

conditions for chromatography: chromatographic column: Agilent J&W Scientific HP-5 capillary chromatographic column (30 m×0.25 mm, 0.25 μm); the column temperature is increased according to the following temperature programming: initial temperature is 98° C., the temperature is kept for 12 minutes, increased to 140° C. at a rate of 8° C. per minute, kept for 2.5 minutes, then increased to 280° C. at a rate of 140° C. per minute, kept for 5-20 minutes; detector temperature is 350° C.; inlet temperature is 350° C.; carrier gas is nitrogen, flow rate: 0.8 mL/min; injection by split injection, split ratio: 25:1; the volume of injected sample: 0.5 μL; fuel gas ratio: air-hydrogen (450:45);

determination method: accurately taking 0.5 μL of the solution of menthol reference substance and 0.5 μL of the test solution, respectively, injecting the solutions into a gas chromatograph, determining then obtaining the results.

Optionally, the method for determining the content of the present invention is as follows:

test solution preparation: taking the substance contained in the composition from the samples of loading difference test, grinding finely, mixing evenly, taking 0.5 g, accurately weighing, placing in a conical flask equipped with a plug, adding 30 mL of n-hexane accurately, shaking the flask clockwise and counterclockwise for about 50 seconds, taking a suitable amount of solution, filtering through a 0.22 μm microporous membrane to obtain the test solution;

preparation of the solution of reference substance: taking a suitable amount of menthol reference substance, weighing accurately, adding n-hexane to prepare a menthol solution with a menthol concentration of 0.23 mg per 1 mL of n-hexane to obtain the solution of menthol reference substance;

conditions for chromatography: chromatographic column: Agilent J&W Scientific HP-5 capillary chromatographic column (30 m×0.25 mm, 0.25 μm); the column temperature is increased according to the following temperature programming: initial temperature 98° C., the temperature is kept for 12 minutes, increased to 140° C. at a rate of 8° C. per minute, kept for 2.5 minutes, then increased to 280° C. at a rate of 140° C. per minute, kept for 5-20 minutes; detector temperature is 400° C.; inlet temperature is 400° C.; carrier gas is nitrogen, flow rate: 1.2 mL/min; injection by split injection, split ratio: 25:1; the volume of injected sample: 2 μL; fuel gas ratio: air-hydrogen (450:45);

determination method: accurately taking 2 μL of the solution of menthol reference substance and 2 μL of the test solution, respectively, injecting the solutions into a gas chromatograph, determining then obtaining the results.

Test Method Feasibility Evaluation

The feasibility evaluation of the method for determining the content of the traditional Chinese medicine composition of the present invention was carried out using the preparation of the traditional Chinese medicine composition prepared in the first embodiment of the present invention, and the method for the evaluation was as follows:

1. Instruments, Reagents and Medicine

Instruments: PerKinElmer Clarus 680 Gas Chromatograph, AL204 and AB135-S Electronic Balances, Agilent J&W Scientific HP-5 Capillary Chromatographic Columns (30 m×0.25 mm, 0.25 μm), Computerized Numerical Control Ultrasonic Cleaner (Model: KQ-500DB, 500 W, 40 KHZ), 0.22 μm microporous membrane (Tianjin Jinteng Experimental Equipment Co., Ltd.).

Reagents: n-hexane (chromatographic grade, Fisher, U.S.), petroleum ether, dichloromethane, ethyl acetate (analytical grade, Beijing Chemical Plant).

Medicine: menthol reference substance (purchased from SIGMA-ALORICH, lot number: M2772-100G-A, purity 99%).

2. Conditions for Chromatography

Chromatographic column: Agilent J&W Scientific HP-5 capillary chromatographic column (30 m×0.25 mm, 0.25 μm); the column temperature was increased according to the following temperature programming: initial temperature was 98° C., the temperature was kept for 12 minutes, increased to 140° C. at a rate of 8° C. per minute, kept for 2.5 minutes, then increased to 280° C. at a rate of 140° C. per minute, kept for 10 minutes; detector temperature was 300° C.; inlet temperature was 300° C.; carrier gas was nitrogen, flow rate: 1 mL/min; injection by split injection, split ratio: 25:1; the volume of injected sample: 1 μL; fuel gas ratio: air-hydrogen (450:45).

3. Preparations of Test Solution and the Solution of Menthol Reference Substance 3.1 Study on the Method for Preparing the Test Solution 3.1.1 Study on Solvents for Extraction The substance contained in the traditional Chinese composition from the samples of loading difference test was taken, ground finely, mixed evenly, 0.3 g of the obtained substance was collected, weighed accurately, placed in a 100 ml conical flask equipped with a plug, 2 samples were prepared in parallel with 50 mL of each of the following solvents for extraction: petroleum ether, dichloromethane, n-hexane, ethyl acetate. Petroleum ether, dichloromethane, n-hexane, ethyl acetate were accurately taken (60-90° C.) respectively, the flask was shook clockwise and counterclockwise for about 30 seconds, a suitable amount of solution was taken, filtered through a 0.22 μm microporous membrane to obtain a test solution.

1 μL of each of the test solution was taken respectively, injected into a gas chromatograph, the menthol reference substance was used as a control sample, the percentages of menthol in the test solution were compared. The results showed that when n-hexane was used as the solvent for extraction, the percentage of the content to be tested was relatively high, thus n-hexane was selected as the solvent for extraction (Table 1).

TABLE 1

Results of the study of solvents for extraction (n = 2)

| Solvents | Percentages (%) |
| --- | --- |
| Petroleum ether | 1.90 |
| Dichloromethane | 1.91 |
| N-hexane | 1.93 |
| Ethyl acetate | 1.83 |

3.1.2 Study on Methods for Extraction

The substance contained in the traditional Chinese composition was taken from the samples of loading difference test, ground finely, mixed evenly, 0.3 g was taken, weighed accurately and placed in a 100 ml conical flask equipped with a plug. 2 samples were prepared by cold soaking extraction (i.e., soaking extraction at room temperature) and ultrasonic extraction in parallel, respectively. Cold soaking extraction: 50 mL of n-hexane was taken accurately, after 20 minutes of cold soaking, shook clockwise and counterclockwise for 30 seconds; ultrasonic extraction: 50 mL of n-hexane was taken accurately, weighed before ultrasonic treatment, 20 minutes after ultrasonic treatment, n-hexane was added to replenish the weight. A suitable amount of solution was taken from each extraction method, filtered through a 0.22 μm microporous membrane to obtain a test solution;

1 μL of each of test solutions was taken respectively, injected into a gas chromatograph, a menthol reference substance was used as a control sample, the percentages of menthol in test solutions were compared. The results showed that the effects of the two extraction methods were similar. Cold extraction was selected considering the convenience thereof (Table 2).

TABLE 2

Results of the study of methods for extraction (n = 2)

| Methods for extraction | Percentages (%) |
|---|---|
| Cold soaking | 1.93 |
| Ultrasonic | 1.96 |

3.1.3 Study on Times for Extraction

The substance contained in the traditional Chinese composition was taken from the samples of loading difference test, ground finely, mixing evenly, 0.3 g was taken, accurately weighed, placed in a 100 ml conical flask equipped with a plug, cold soaking extraction times were 0 minute, 20 minutes, 40 minutes respectively, 2 samples were prepared for each extraction time, the flask was shook clockwise and counterclockwise for about 30 seconds, a suitable amount of solution was taken, filtered through a 0.22 μm microporous membrane to obtain a test solution.

1 μL of each the test solutions was taken respectively, injected into a gas chromatograph, menthol reference substance was used as a control sample, the percentages of menthol in test solutions were compared. The results showed that the percentages of menthol obtained from the three extraction times were similar, therefore, 0 minute of cold soaking was selected (Table 3).

TABLE 3

Results of the study of extraction times (n = 2)

| Times (min) | Percentages (%) |
|---|---|
| 0 | 1.94 |
| 20 | 1.96 |
| 40 | 1.93 |

3.1.4 Study on the Amounts of Solvents

The substance contained in the traditional Chinese composition was taken from the samples of loading difference test, ground finely, mixed evenly, 0.3 g was taken, weighed accurately, placed in a conical flask equipped with a plug, 2 samples for each amount of solvent were prepared in parallel, the amounts of solvents that were taken accurately were: 25 mL, 50 mL and 75 mL, the flask was shaken clockwise and counterclockwise for about 30 seconds, a suitable amount of solution was taken, filtered through a 0.22 μm microporous membrane to obtain a test solution.

1 μL of test solution was taken respectively, injected into a gas chromatograph, menthol reference substance was used as a control sample, the percentages of menthol in the test solutions were compared. Results showed that the effects of extraction obtained from 25 mL, 50 mL and 75 mL were similar, therefore the amount of solvent selected was 25 mL (Table 4).

TABLE 4

Results of the study of the amounts of solvents (n = 2)

| Amounts of solvents (mL) | Percentages (%) |
|---|---|
| 25 | 1.87 |
| 50 | 1.90 |
| 75 | 1.87 |

3.1.5 Determination on the Method for Preparation a Test Solution

According to the above test results, the method for preparing the test solution was finally determined as follows: taking the substance contained in the traditional Chinese composition from the samples of loading difference test, grinding finely, mixing evenly, taking 0.3 g, accurately weighing, placing in a conical flask equipped with a plug, accurately adding 25 mL of n-hexane, shaking the flask clockwise and counterclockwise for about 30 seconds, taking a suitable amount of solution, filtering through a 0.22 μm microporous membrane to obtain a test solution.

3.2 Study on the Method for Preparing the Solution of Menthol Reference Substance Preparation of the Solution of Reference Substance A suitable amount of menthol reference substance was taken and accurately weighed, n-hexane was added to prepare a menthol solution with a concentration of 0.23 mg/1 mL.

3.2.1 Study on Specificity

A solvent (i.e. blank reagent), a negative control solution, the solution of menthol reference substance and the test solution were tested according to the determined conditions, wherein the negative control solution refers to the solution prepared according to the method for preparing the test solution without adding menthol. The results showed that the negative control had no interference affecting the test components and had good specificity for the test components (chromatograms of the solvent, negative control, reference substance, test sample are shown in FIGS. 2 to 5).

3.2.2 Study on Linear Relationship 100.51 mg of menthol reference substance was weighed, placed in a 50 mL volumetric flask and dissolved with n-hexane and n-hexane was added to the metered volume, the obtained mixture was shook evenly and kept the obtained solution for later use, then 1 mL, 1.5 mL, 2 mL, 2.5 mL, 3 mL, 3.5 mL of the solution were taken accurately and placed in a 25 mL volumetric flask, diluted with n-hexane until n-hexane was added to the scale, a series of solutions of menthol reference substance with concentrations of 0.0804 mg/mL, 0.1206 mg/mL, 0.1608 mg/mL, 0.2010 mg/mL, 0.2412 mg/mL and 0.2814 mg/mL were prepared, 1 μL of each of the above solutions of menthol reference substance were taken accurately, injected into a gas chromatograph, peak areas were detected, linear regression was performed with the concentrations of the injected samples (mg/mL) as the x-coordinates and the peak areas as the y-coordinates, the results showed that the linearity was good within the range of menthol concentration from 0.0804 mg/mL to 0.2814 mg/mL, and the regression equation was $y=48583.7941x+142.5821$ ($R^2=0.9996$). The results are shown in Table 5 and FIG. 1.

TABLE 5

Relationship between concentrations of menthol reference substance and peak areas

| Concentrations (mg/mL) | 0.0804 | 0.1206 | 0.1608 | 0.2010 | 0.2412 | 0.2814 |
|---|---|---|---|---|---|---|
| Peak areas (μv*sec) | 4043.77 | 5974.50 | 7959.45 | 9907.99 | 11990.73 | 13717.16 |

3.2.3 Determination of Detection Limit and Quantitation Limit

The solution of menthol reference substance with a concentration of 0.0804 mg/ml was further diluted to a series of solutions of menthol reference substances with concentrations of 28.944 μg/mL, 24.120 μg/mL, 19.296 μg/mL, 17.688 μg/mL, 16.080 μg/mL, 12.060 μg/mL, 8.040 μg/mL, 6.432. μg/mL, 4.824 μg/mL, 3.216 μg/mL, respectively, 1 μL of each of the above solutions of menthol reference substance was taken, injected into a gas chromatograph, the ratio of signal intensity to noise intensity was recorded. The concentration at which the ratio of signal intensity to noise intensity equals to 3 was used as the detection limit. The concentration at which the ratio of signal intensity to noise intensity equals to 10 was used as the quantitation limit. The detection limit and quantitation limit of menthol were 4.824 μg/mL and 17.688 μg/mL, respectively.

4. Methodological Study 4.1 Accuracy Study

A suitable amount of the traditional Chinese medicine composition of the present invention was taken, ground finely, mixed evenly, 0.3 g was taken, weighed accurately, test solutions were prepared according to the method for preparing a test solution, the solution of menthol reference substance (0.2292 mg/ml) was taken, samples were injected for 6 times according to the determined conditions for chromatography, the peak areas of menthol were recorded, and the RSD thereof was calculated. The results are shown in Table 6.

TABLE 6

Results of accuracy study

| Areas (μv × sec) | Times | | | | | | RSD (%) |
|---|---|---|---|---|---|---|---|
| | 1 | 2 | 3 | 4 | 5 | 6 | |
| Peak areas of the reference substance | 10695.33 | 10303.43 | 10536.32 | 10421.35 | 10545.09 | 10419.22 | 1.30 |
| Peak areas of the sample | 10833.94 | 11227.92 | 10918.84 | 11033.49 | 11035.97 | 10902.97 | 1.28 |

The results of Table 6 show peak area RSD of menthol in the test solution and the reference substance solution was less than 2%, indicating a good accuracy of the device 4.2 Stability Test A suitable amount of the traditional Chinese medicine composition of the present invention was taken, ground evenly, 0.3 g was taken, weighed accurately, the test solution was prepared according to the method for preparing the test solution, according to the determined conditions for chromatography, samples were injected at 0 h, 2 h, 4 h, 6 h, 8 h, 10 h, 12 h and 24 h, respectively, peak areas of menthol were recorded, the RSD thereof was calculated and the stability of the solution was studied. The results are shown in Table 7.

TABLE 7

Test results of stability

| Times of injection (h) | Peak areas (μv × sec) |
|---|---|
| 0 | 10259.94 |
| 2 | 10236.74 |
| 4 | 10492.14 |
| 6 | 10494.76 |
| 8 | 10486.51 |
| 10 | 10565.91 |
| 12 | 10506.19 |
| 24 | 11204.67 |
| RSD (%) | 2.83 |

The results in Table 7 show that the RSD of the peak area of menthol in the test solution was less than 3% within 24 hours, indicating that the test solution was stable within 24 hours.

4.3 Repeatability Test

A suitable amount of the traditional Chinese medicine composition of the present invention was taken, ground finely, samples were taken with an amount that is 80%, 100% and 120% of the amounts taken by the method for preparing the test solution, i.e. about 0.24 g, 0.3 g, 0.36 g were taken separately, 3 samples were taken in parallel for each amount, 9 samples in total. The test solution was prepared according to the method for preparing the test solution, the contents (%) of menthol in the test solution were determined and calculated according to the determined conditions for chromatography, the RSD thereof was calculated. The results are shown in Table 8.

TABLE 8

Results of repeatability test

| Sample amounts (g) | Menthol contents (%) | Average menthol content (%) | RSD (%) |
|---|---|---|---|
| 0.2448 | 1.87 | 1.86 | 2.24 |
| 0.2442 | 1.82 | | |
| 0.2456 | 1.87 | | |
| 0.3033 | 1.86 | | |

TABLE 8-continued

Results of repeatability test

| Sample amounts (g) | Menthol contents (%) | Average menthol content (%) | RSD (%) |
|---|---|---|---|
| 0.3050 | 1.94 | | |
| 0.3055 | 1.87 | | |
| 0.3657 | 1.86 | | |
| 0.3658 | 1.79 | | |
| 0.3621 | 1.82 | | |

The results in Table 8 show that the average menthol content in the 9 test solutions was 1.86%, the RSD of the content was less than 3%, indicating that the method has good repeatability.

4.4 Recovery Test

A sample was weighted according to half of 0.3 g of the sample amount, i.e. 0.15 g, weighed accurately, 9 samples were prepared in parallel, the solution of menthol reference substance with a known content was taken, the solutions of menthol reference substance were added to the samples in a ratio of 80%, 100% and 120% of the sample amount, respectively. 3 samples were prepared in parallel, the test solution was prepared according to the method for preparing the test solution, determined according to the determined conditions for chromatography, the recovery of the menthol in the traditional Chinese medicine composition was calculated, and the RSD thereof was calculated. The results are shown in Table 9.

TABLE 9

Test recovery results of menthol

| Sample amounts (g) | Sample contents (mg) | Amounts of added reference substance (mg) | Actual amounts of sample with added reference substance (mg) | Recoveries (%) | Average recovery (%) | RSD (%) |
|---|---|---|---|---|---|---|
| 0.1512 | 2.8123 | 2.2272 | 4.9839 | 97.50 | 97.68 | 2.49 |
| 0.1545 | 2.8737 | 2.2272 | 5.1344 | 101.50 | | |
| 0.1540 | 2.8644 | 2.2272 | 5.1349 | 101.94 | | |
| 0.1526 | 2.8384 | 2.784 | 5.5211 | 96.36 | | |
| 0.1536 | 2.8570 | 2.784 | 5.5718 | 97.52 | | |
| 0.1539 | 2.8625 | 2.784 | 5.5517 | 96.60 | | |
| 0.1544 | 2.8718 | 3.3408 | 6.1122 | 96.99 | | |
| 0.1511 | 2.8105 | 3.3408 | 6.0039 | 95.59 | | |
| 0.1555 | 2.8923 | 3.3408 | 6.0700 | 95.12 | | |

The results in Table 9 show that the average value of the menthol recovery in the nine test solutions was 97.68%, the RSD thereof was 2.4%, indicating that the method has good recovery.

4.5 System Suitability Test 4.5.1 Influence of Carrier Gas Flow Rate on Menthol Content Determination A suitable amount of the traditional Chinese medicine composition of the present invention was taken, ground finely, mixed evenly, 0.3 g was taken, accurately weighted, 2 samples were provided in parallel, the test solution was prepared according to the method for preparing the test solution, the other conditions for chromatography were fixed, measurements were taken at the carrier gas flow rate of 0.80, 1.00 and 1.20 mL/minute (two injections were injected in parallel for each sample), respectively, menthol reference substance was used as reference substance, the content of the menthol in the traditional Chinese medicine composition was calculated, the influence of the carrier gas flow rate change on the measurement results were compared. The results are shown in Table 10.

TABLE 10

Influence of carrier gas flow rate change on menthol content

| Carrier gas flow rate (mL/min) | Menthol content (%) | Average content (%) | RSD (%) |
|---|---|---|---|
| 0.80 | 1.91 | 1.92 | 0.65 |
| 1.00 | 1.93 | | |
| 1.20 | 1.92 | | |

It can be seen from the above results that after the change of the carrier gas flow rate, the RSD value of the menthol content measurement results was less than 3%, indicating that the change of the carrier gas flow rate has little influence on the measurement results of the sample contents.

4.5.2 Influence of Detector Temperature Change on Determination of Menthol Content The test solution was taken, other conditions for chromatography were fixed, measurements were taken at the FID detector temperatures of 295° C., 300° C. and 305° C., respectively, and the menthol reference substance was used as a reference substance, the content of menthol in the traditional Chinese medicine composition of the present invention was calculated, the influences of the FID detector temperature change on measurement results were compared. The results are shown in Table 11.

TABLE 11

Influence of FID detector temperature change on menthol content

| Detector temperature (° C.) | Menthol content (%) | Average content (%) | RSD (%) |
|---|---|---|---|
| 295 | 1.91 | 1.93 | 1.13 |
| 300 | 1.94 | | |
| 305 | 1.95 | | |

It can be seen from the above results that after the change of detector temperature, the RSD value of the menthol content measurement result was less than 3%, indicating that the change of detector temperature has little influence on the measurement results of the sample contents.

4.5.3 Influence of Inlet Temperature Change on Menthol Content Determination

The test solution was taken, other conditions for chromatography were fixed, measurements were taken at inlet temperatures of 295° C., 300° C. and 305° C., respectively, and the menthol reference substance was used as a reference substance, the content of menthol in the traditional Chinese medicine composition of the present invention was calculated, the influences of the inlet temperature change on measurement results were compared. The results are shown in Table 12.

TABLE 12

Influence of inlet temperature change on menthol content

| Inlet temperature (° C.) | Menthol content (%) | Average content (%) | RSD (%) |
|---|---|---|---|
| 295 | 1.91 | 1.93 | 1.13 |
| 300 | 1.94 | | |
| 305 | 1.95 | | |

It can be seen from the above results that after the change of inlet temperature, the RSD value of the menthol content measurement result was less than 3%, indicating that the change of inlet temperature has little influence on the sample content measurement results.

4.5.3 Influence of Different Capillary Chromatographic Columns on Menthol Content Determination The test solution was taken, other conditions for chromatography were fixed, measurements were taken using different capillary chromatographic columns Agilent DB-5 and Agilent HP-5, respectively, and the menthol reference substance was used as a reference substance, the content of menthol in the traditional Chinese medicine composition of the present invention was calculated, the influences of the chromatographic columns on measurement results were compared. The results are shown in Table 13.

TABLE 13

Influence of the chromatographic columns on measurement results

| Types of chromatographic columns | Menthol content (%) | Average content (%) | RD (%) |
|---|---|---|---|
| DB-5 | 1.91 | 1.90 | 0.35 |
| HP-5 | 1.90 | | |

It can be seen from the above results that when different types of capillary chromatographic columns of the same brand were selected, the RD value of the menthol content measurement result was less than 3%, indicating that this content determination method has good suitability.

4.5.4 Results of the Content Determination of Menthol in Different Batches of Traditional Chinese Medicine Compositions of the Present Invention The menthol contained in 10 batches of the traditional Chinese medicine composition of the present invention (the table below) from Yiling Pharmaceutical Co., Ltd. in Shijiazhuang was determined by the method for determining the content. The results are shown in Table 14.

TABLE 14

Results of determining the content of menthol in 10 batches of the preparations of the traditional Chinese medicine composition of the present invention

| Batch No. | Menthol contents (%) |
|---|---|
| A1601015 | 1.88 |
| A1602014 | 1.87 |
| A1601030 | 1.95 |
| A1601028 | 1.85 |
| A1602012 | 1.81 |
| A1601018 | 1.84 |
| A1602011 | 1.94 |
| A1602009 | 1.91 |
| A1601022 | 1.83 |
| A1601020 | 1.93 |

A method for determining the content of menthol in the traditional Chinese medicine composition of the invention is established, and the above experimental results show that the method has good accuracy, stability, and repeatability, and provides a new method to improve the quality control of the traditional Chinese medicine composition.

DETAILED DESCRIPTION

Devices and Reagents

Figure 1:
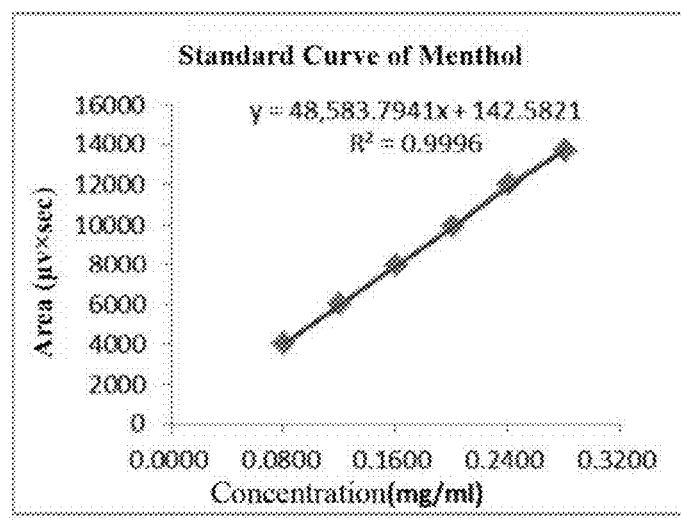
FIG. 1: standard curve of menthol
Figure 2:
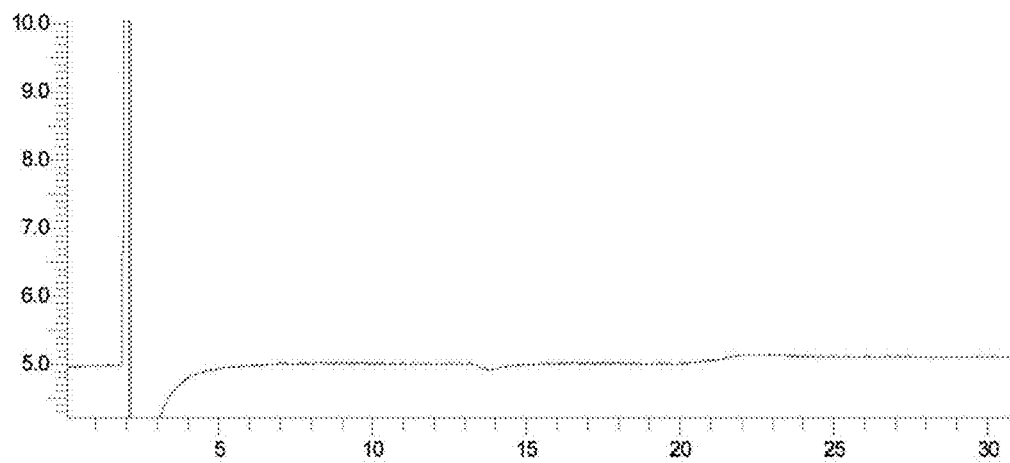
FIG. 2: the chromatogram of the blank reagent
Figure 3:
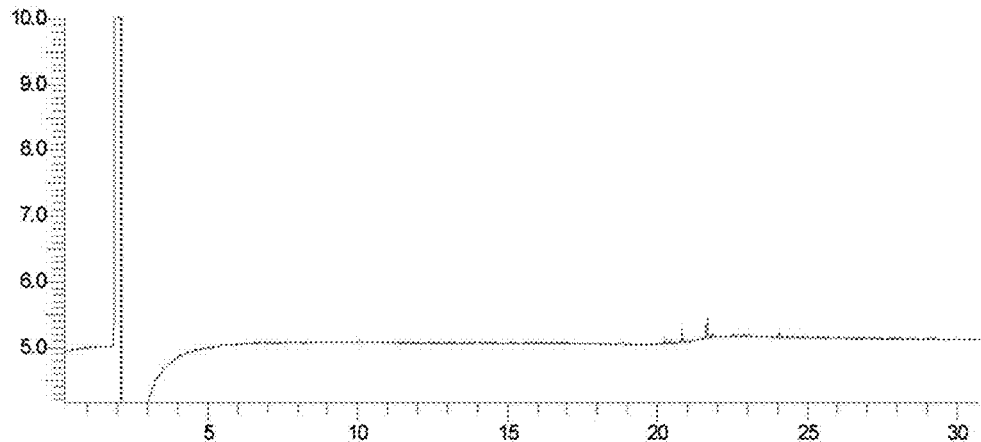
FIG. 3: the chromatogram of the negative reference substance solution
Figure 4:
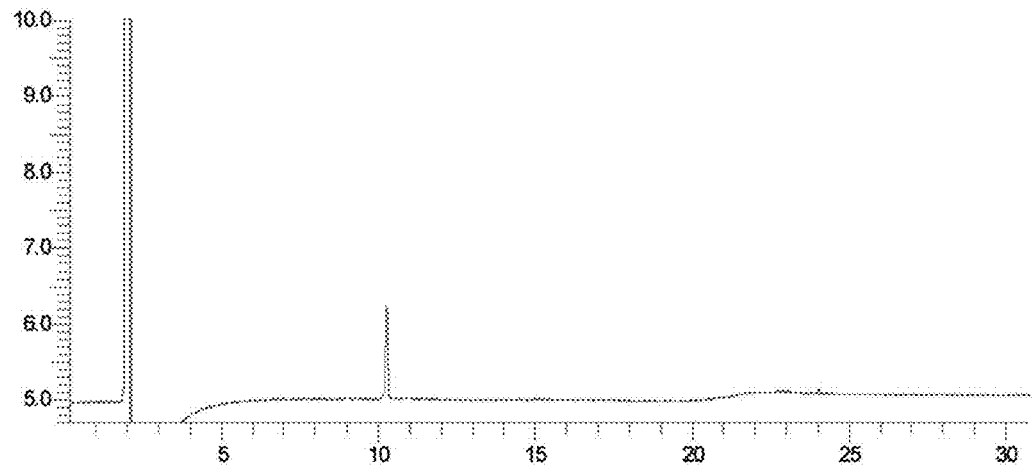
FIG. 4: the chromatogram of the solution of reference substance
Figure 5:
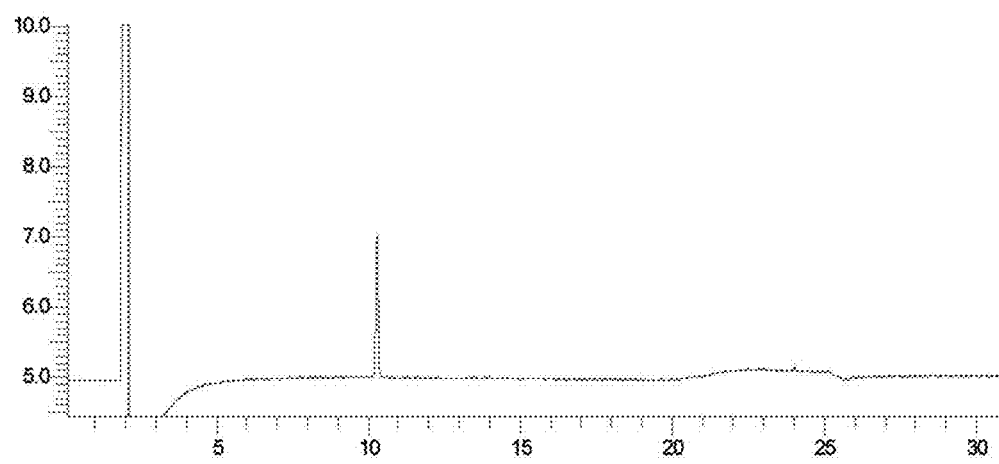
FIG. 5: the chromatogram of the test solution

Device: PerKinElmer Clarus 680 Gas Chromatograph, AL204 and AB135-S type Electronic Balances, Agilent J&W Scientific HP-5 Capillary Chromatographic Columns (30 m×0.25 mm, 0.25 μm), Computerized Numerical Control Ultrasonic Cleaner (Model: KQ-500DB, 500 W, 40 KHZ), 0.22 μm microporous membrane (Tianjin Jinteng Experimental Equipment Co., Ltd.).

Reagents: n-hexane (chromatographic grade, Fisher, U.S.), petroleum ether, dichloromethane, ethyl acetate (analytical grade, Beijing Chemical Plant).

Medicine: menthol reference substance (purchased from SIGMA-ALORICH, lot number: M2772-100G-A, purity is 99%).

Each of the following examples was carried out for three times in parallel in accordance with the listed conditions, and the numbers were recorded as 1, 2 and 3, respectively.

EXAMPLE 1

The following materials were weighed according to the ratio below: *Fructus Forsythia* 200, *Flos Lonicerae* 300, *Radix Isatidis* 200, *rheum* 40, *Herba Pogostemonis* 60, *Rhizoma Dryopteris Crassirhizomae* 300, *Rhodiola rosea* L. 100, menthol 9, *Herba Ephedrae* 60, *Semen Armeniacae Amarum* 100, *Herba Houttuyniae* 200, *Radix Glycyrrhizae* 100 and *gypsum* 200, were extracted according to the following process:

(1) the traditional Chinese medicines were weighed according to the weight ratio of raw materials, the medicinal parts were selected and processed into pieces as required;

(2) *Herba Pogostemonis* was processed into pieces, water was added (the ratio of the volume of water to the weight of medicinal material (L/kg, mL/g) was 10) to extract volatile oil, oil extraction time: 8 hours, the volatile oil was collected for later use; after the extract was filtered, the residue was removed, the filtrate was kept for later use;

(3) *Fructus Forsythia*, *Herba Ephedrae*, *Herba Houttuyniae* and *rheum* were extracted with 70% ethanol (the ratio of the volume of water to the weight of medicinal material (L/kg, mL/g) was 12) for 3 times, and each extraction took 2.5 hours, the extracts were combined and filtered, the ethanol was recycled, the filtrate was kept for later use;

(4) water was added to *Flos Lonicerae*, *gypsum*, *Radix Isatidis*, *Rhizoma Dryopteris Crassirhizomae*, *Radix Glycyrrhizae* and *Rhodiola rosea* L. (the ratio of the volume of the water to the weight of the medicinal material (L/kg, mL/g) was 12) and the obtained mixture was decocted until the mixture was boiled, *Semen Armeniacae Amarum* was added, the obtained mixture was decocted for 2 times, each decoction took 1 hour, the extracts were combined and filtered, the obtained filtrate was combined with the filtrate obtained after the oil extraction of *Herba Pogostemonis* in step (2), the obtained combination was concentrated to obtain a clear paste with a relative density of 1.15 determined at 60° C., ethanol was added, the obtained mixture was adjusted to an alcohol concentration of 70%, refrigerated, filtered, the ethanol was recycled until there's no smell of alcohol, a clear paste was obtained for later use;

(5) the clear paste obtained in step (4) was combined with the ethanol extract in step (3), the obtained combination was concentrated to obtain a clear paste with a relative density of 1.20 determined at 60° C., the clear paste was dried to obtain dry paste powders for later use;

(6) the dry paste powders obtained in step (5) was added to a suitable pharmaceutically acceptable auxiliary material for granulation; the auxiliary material can be 35 g of starch;

(7) menthol and the volatile oil obtained in step (2) were added to ethanol and allowing the menthol and volatile oil dissolved in ethanol, the granules obtained in step (6) were sprayed into the obtained mixture, the product was obtained after encapsulating.

The method for determining the content of menthol:

test solution preparation: the substance contained in the composition from the samples of loading difference test was taken, ground finely, mixed evenly, 0.3 g was taken, weighed accurately, placed in a conical flask equipped with a plug, 25 mL of n-hexane was added accurately, the flask was shaken clockwise and counterclockwise for about 30 seconds, a suitable amount of solution was taken, filtered through a 0.22 μm microporous membrane to obtain the test solution;

preparation of the solution of reference substance: a suitable amount of menthol reference substance was taken, weighed accurately, n-hexane was added to prepare a menthol solution with a menthol concentration of 0.23 mg per 1 mL to obtain the solution of menthol reference substance;

conditions for chromatography: chromatographic column: Agilent J&W Scientific HP-5 capillary chromatographic column (30 m×0.25 mm, 0.25 μm); the column temperature was increased according to the following temperature programming: initial temperature of 98° C., the temperature was kept for 12 minutes, increased to 140° C. at a rate of 8° C. per minute, kept for 2.5 minutes, then increased to 280° C. at a rate of 140° C. per minute, kept for 10 minutes; detector temperature was 300° C.; inlet temperature was 300° C.; carrier gas was nitrogen, flow rate: 1 mL/min; injected by split injection, split ratio: 25:1; the volume of injected sample: 1 μL; fuel gas ratio: air-hydrogen (450:45);

determination method: 1 μL of the solution of menthol reference substance and the test solution were accurately taken, respectively, and were injected into a gas chromatograph, were determined to obtain the results.

Results of the Determination of Menthol Content in the Composition

| No. | Menthol contents (%) |
| --- | --- |
| 1 | 1.98 |
| 2 | 1.92 |
| 3 | 1.95 |

Conclusion: the result is that the menthol was well separated and can be used to control the quality of the traditional Chinese medicine composition.

EXAMPLE 2

The following materials were weighed according to the ratio below: *Fructus Forsythia* 300, *Flos Lonicerae* 200, *Radix Isatidis* 300, *rheum* 60, *Herba Pogostemonis* 100, *Rhizoma Dryopteris Crassirhizomae* 200, *Rhodiola rosea* L. 60, menthol 5, *Herba Ephedrae* 100, *Semen Armeniacae Amarum* 60, *Herba Houttuyniae* 300, *Radix Glycyrrhizae* 60 and *gypsum* 300, were extracted according to the following process:

(1) the traditional Chinese medicines were weighed according to the weight ratio of raw materials, the medicinal parts were selected and processed into pieces as required;

(2) *Herba Pogostemonis* was processed into pieces, water was added (the ratio of the volume of water to the weight of medicinal material (L/kg, mL/g) was 10) to extract volatile oil, oil extraction time: 8 hours, the volatile oil was collected for later use; after the extract was filtered, the residue was removed, the filtrate was kept for later use;

(3) *Fructus Forsythia*, *Herba Ephedrae*, *Herba Houttuyniae* and *rheum* were extracted with 70% ethanol (the ratio of the volume of water to the weight of medicinal material (L/kg, mL/g) was 12) for 3 times and each extraction took 2.5 hours, the extracts were combined and filtered, the ethanol was recycled, the filtrate was kept for later use;

(4) water was added to *Flos Lonicerae*, *gypsum*, *Radix Isatidis*, *Rhizoma Dryopteris Crassirhizomae*, *Radix Glycyrrhizae* and *Rhodiola rosea* L. (the ratio of the volume of the water to the weight of the medicinal material (L/kg, mL/g) was 12) and the obtained mixture was decocted until the mixture was boiled, *Semen Armeniacae Amarum* was added, the obtained mixture was decocted for 2 times, each decoction took 1 hour, the extracts were combined and filtered, the obtained filtrate was combined with the filtrate obtained after the oil extraction of *Herba Pogostemonis* in step (2), the obtained combination was concentrated to obtain a clear paste with a relative density of 1.10 determined at 60° C., ethanol was added, the obtained mixture was adjusted to an alcohol concentration of 70%, refrigerated, filtered, the ethanol was recycled until there's no smell of alcohol, a clear paste was obtained for later use;

(5) the clear paste obtained in step (4) was combined with the ethanol extract in step (3), the obtained combination was concentrated to obtain a clear paste with a relative density of 1.15 determined at 60° C., the clear paste was dried to obtain dry paste powders for later use;

(6) the dry paste powders obtained in step (5) was added to a suitable pharmaceutically acceptable auxiliary material for granulation; the auxiliary material can be 35 g of starch;

(7) menthol and the volatile oil obtained in step (2) were added to ethanol and allowing the menthol and volatile oil dissolved in ethanol, the granules obtained in step (6) were sprayed into the obtained mixture, the product was obtained after tabletting.

The method for determining the content of menthol:

test solution preparation: the substance contained in the composition from the samples of loading difference test was taken, ground finely, mixed evenly, 0.2 g was taken, weighed accurately, placed in a conical flask equipped with a plug, 20 mL of n-hexane was added accurately, the flask was shaken clockwise and counterclockwise for about 20 seconds, a suitable amount of solution was taken, filtered through a 0.22 μm microporous membrane to obtain the test solution;

preparation of the solution of reference substance: a suitable amount of menthol reference substance was taken, weighed accurately, n-hexane was added to prepare a menthol solution with a menthol concentration of 0.23 mg per 1 mL of n-hexane to obtain the solution of menthol reference substance;

Conditions for chromatography: chromatographic column: Agilent J&W Scientific HP-5 capillary chromatographic column (30 m×0.25 mm, 0.25 μm); the column temperature was increased according to the following temperature programming: initial temperature was 98° C., the temperature was kept for 12 minutes, increased to 140° C. at a rate of 8° C. per minute, kept for 2.5 minutes, then increased to 280° C. at a rate of 140° C. per minute, kept for 5-20 minutes; detector temperature was 350° C.; inlet temperature was 350° C.; carrier gas was nitrogen, flow rate: 0.8 mL/min; injected by split injection, split ratio: 25:1; the volume of injected sample: 0.5 μL; fuel gas ratio: air-hydrogen (450:45);

determination method: 0.5 μL of the solution of menthol reference substance and the test solution were accurately taken, respectively, and were injected into a gas chromatograph, were determined to obtain the results.

Results of the Determination of Menthol Content in the Composition

| No. | Menthol contents (%) |
|---|---|
| 1 | 1.28 |
| 2 | 1.36 |
| 3 | 1.24 |

Conclusion: the result is that the menthol was well separated and can be used to control the quality of the traditional Chinese medicine composition.

EXAMPLE 3

The following materials were weighed according to the ratio below: *Fructus Forsythia* 278, *Flos Lonicerae* 294, *Radix Isatidis* 285, *rheum* 55, *Herba Pogostemonis* 95, *Rhizoma Dryopteris Crassirhizomae* 290, *Rhodiola rosea* L. 87, menthol 8.5, *Herba Ephedrae* 88, *Semen Armeniacae Amarum* 80, *Herba Houttuyniae* 284, *Radix Glycyrrhizae* 95 and *gypsum* 277, were extracted according to the following process:

(1) the traditional Chinese medicines were weighed according to the weight ratio of raw materials, the medicinal parts were selected and processed into pieces as required;

(2) *Herba Pogostemonis* was processed into pieces, water was added (the ratio of the volume of water to the weight of medicinal material (L/kg, mL/g) was 10) to extract volatile oil, oil extraction time: 8 hours, the volatile oil was collected for later use; after the extract was filtered, the residue was removed, the filtrate was kept for later use;

(3) *Fructus Forsythia*, *Herba Ephedrae*, *Herba Houttuyniae* and *rheum* were extracted with 70% ethanol (the ratio of the volume of water to the weight of medicinal material (L/kg, mL/g) was 12) for 3 times, and each extraction took 2.5 hours, the extracts were combined and filtered, the ethanol was recycled, the filtrate was kept for later use;

(4) water was added to *Flos Lonicerae*, *gypsum*, *Radix Isatidis*, *Rhizoma Dryopteris Crassirhizomae*, *Radix Glycyrrhizae* and *Rhodiola rosea* L. (the ratio of the volume of the water to the weight of the medicinal material (L/kg, mL/g) was 12) and the obtained mixture was decocted until the mixture was boiled, *Semen Armeniacae Amarum* was added, the obtained mixture was decocted for 2 times, each decoction took 1 hour, the extracts were combined and filtered, the obtained filtrate was combined with the filtrate obtained after the oil extraction of *Herba Pogostemonis* in step (2), the obtained combination was concentrated to obtain a clear paste with a relative density of 1.13 determined at 60° C., ethanol was added, the obtained mixture was adjusted to an alcohol concentration of 70%, refrigerated, filtered, the ethanol was recycled until there's no smell of alcohol, a clear paste was obtained for later use;

(5) the clear paste obtained in step (4) was combined with the ethanol extract in step (3), the obtained combination was concentrated to obtain a clear paste with a relative density of 1.18 determined at 60° C., the clear paste was dried to obtain dry paste powders for later use;

(6) the dry paste powders obtained in step (5) was added to a suitable pharmaceutically acceptable auxiliary material for granulation; the auxiliary material can be 35 g of starch;

(7) menthol and the volatile oil obtained in step (2) were added to ethanol and allowing the menthol and volatile oil dissolved in ethanol, the granules obtained in step (6) were sprayed into the obtained mixture, the product was obtained after bagging.

The method for determining the content of menthol:

test solution preparation: the substance contained in the composition from the samples of loading difference test was taken, ground finely, mixed evenly, 0.5 g was taken, weighed accurately, placed in a conical flask equipped with a plug, 30 mL of n-hexane was added accurately, the flask was shaken clockwise and counterclockwise for about 50 seconds, a suitable amount of solution was taken, filtered through a 0.22 μm microporous membrane to obtain the test solution;

preparation of the solution of reference substance: a suitable amount of menthol reference substance was taken, weighed accurately, n-hexane was added to prepare a menthol solution with a menthol concentration of 0.23 mg per 1 mL of n-hexane to obtain the solution of menthol reference substance;

Conditions for chromatography: chromatographic column: Agilent J&W Scientific HP-5 capillary chromatographic column (30 m×0.25 mm, 0.25 μm); the column temperature was increased according to the following temperature programming: initial temperature 98° C., the temperature was kept for 12 minutes, increased to 140° C. at a rate of 8° C. per minute, kept for 2.5 minutes, then increased to 280° C. at a rate of 140° C. per minute, kept for 5-20 minutes; detector temperature was 400° C.; inlet temperature was 400° C.; carrier gas was nitrogen, flow rate: 1.2 mL/min; injected by split injection, split ratio: 25:1; the volume of injected sample: 2 µL; fuel gas ratio: air-hydrogen (450:45);

determination method: 2 µL of the solution of menthol reference substance and the test solution were accurately taken, respectively, and were injected into a gas chromatograph, were determined to obtain the results.

Results of the Determination of Menthol Content in the Composition

| No. | Menthol contents (%) |
|---|---|
| 1 | 1.85 |
| 2 | 1.78 |
| 3 | 1.72 |

Conclusion: the result is that the menthol was well separated and can be used to control the quality of the traditional Chinese medicine composition.

EXAMPLE 4

The following materials were weighed according to the ratio below: *Fructus Forsythia* 255, *Flos Lonicerae* 255, *Radix Isatidis* 255, *rheum* 51, *Herba Pogostemonis* 85, *Rhizoma Dryopteris Crassirhizomae* 255, *Rhodiola rosea* L. 85, menthol 7.5, *Herba Ephedrae* 85, *Semen Armeniacae Amarum* 85, *Herba Houttuyniae* 255, *Radix Glycyrrhizae* 85 and *gypsum* 255, were extracted according to the following process:

(1) the traditional Chinese medicines were weighed according to the weight ratio of raw materials, the medicinal parts were selected and processed into pieces as required; (2) *Herba Pogostemonis* was processed into pieces, water was added (the ratio of the volume of water to the weight of medicinal material (L/kg, mL/g) was 10) to extract volatile oil, oil extraction time: 8 hours, the volatile oil was collected for later use; after the extract was filtered, the residue was removed, the filtrate was kept for later use;

(3) *Fructus Forsythia, Herba Ephedrae, Herba Houttuyniae* and *rheum* were extracted with 70% ethanol (the ratio of the volume of water to the weight of medicinal material (L/kg, mL/g) was 12) for 3 times, and each extraction took 2.5 hours, the extracts were combined and filtered, the ethanol was recycled, the filtrate was kept for later use;

(4) water was added to *Flos Lonicerae, gypsum, Radix Isatidis, Rhizoma Dryopteris Crassirhizomae, Radix Glycyrrhizae* and *Rhodiola rosea* L. (the ratio of the volume of the water to the weight of the medicinal material (L/kg, mL/g) was 12) and the obtained mixture was decocted until the mixture was boiled, *Semen Armeniacae Amarum* was added, the obtained mixture was decocted for 2 times, each decoction took 1 hour, the extracts were combined and filtered, the obtained filtrate was combined with the filtrate obtained after the oil extraction of *Herba Pogostemonis* in step (2), the obtained combination was concentrated to obtain a clear paste with a relative density of 1.14 determined at 60° C., ethanol was added, the obtained mixture was adjusted to an alcohol concentration of 70%, refrigerated, filtered, the ethanol was recycled until there's no smell of alcohol, a clear paste was obtained for later use;

(5) the clear paste obtained in step (4) was combined with the ethanol extract in step (3), the obtained combination was concentrated to obtain a clear paste with a relative density of 1.19 determined at 60° C., the clear paste was dried to obtain dry paste powders for later use;

(6) the dry paste powders obtained in step (5) was added to a suitable pharmaceutically acceptable auxiliary material for granulation; the auxiliary material can be 35 g of starch;

(7) menthol and the volatile oil obtained in step (2) were added to ethanol and allowing the menthol and volatile oil dissolved in ethanol, the granules obtained in step (6) were sprayed into the obtained mixture, the product is obtained after encapsulating.

The method for determining the content of menthol:

test solution preparation: the substance contained in the composition from the samples of loading difference test was taken, ground finely, mixed evenly, 0.4 g was taken, weighed accurately, placed in a conical flask equipped with a plug, 20 mL of n-hexane was added accurately, the flask was shaken clockwise and counterclockwise for about 40 seconds, a suitable amount of solution was taken, filtered through a 0.22 µm microporous membrane to obtain the test solution;

preparation of the solution of reference substance: a suitable amount of menthol reference substance was taken, weighed accurately, n-hexane was added to prepare a menthol solution with a menthol concentration of 0.23 mg per 1 mL to obtain the solution of menthol reference substance;

conditions for chromatography: chromatographic column: Agilent J&W Scientific HP-5 capillary chromatographic column (30 m×0.25 mm, 0.25 µm); the column temperature was increased according to the following temperature programming: initial temperature 98° C., the temperature was kept for 12 minutes, increased to 140° C. at a rate of 8° C. per minute, kept for 2.5 minutes, then increased to 280° C. at a rate of 140° C. per minute, kept for 5-20 minutes; detector temperature was 350° C.; inlet temperature was 350° C.; carrier gas was nitrogen, flow rate: 1.1 mL/min; injected by split injection, split ratio: 25:1; the volume of injected sample: 1 µL; fuel gas ratio: air-hydrogen (450:45);

determination method: 1 µL of the solution of menthol reference substance and the test solution were accurately taken, respectively, and were injected into a gas chromatograph, were determined to obtain the results.

Results of the Determination of Menthol Content in the Composition

| No. | Menthol contents (%) |
|---|---|
| 1 | 1.63 |
| 2 | 1.61 |
| 3 | 1.57 |

Conclusion: the result is that the menthol was well separated and can be used to control the quality of the traditional Chinese medicine composition.

What is claimed is:

1. A method for determining the content of menthol in a preparation of a traditional Chinese medicine composition, the preparation of a traditional Chinese medicine composition is prepared from the following raw materials with the following parts by weight: *Fructus Forsythia* 200-300, *Herba Ephedrae* 60-100, rheum 40-60, *Herba Houttuyniae* 200-300, *Flos Lonicerae* 200-300, *Radix Isatidis* 200-300, *Herba Pogostemonis* 60-100, *Rhizoma Dryopteris Crassirhizomae* 200-300, *Rhodiola rosea* L. 60-100, menthol 5-9, *Semen Armeniacae Amarum* 60-100, *Radix Glycyrrhizae* 60-100 and *gypsum* 200-300, wherein the content of the menthol is determined according to the method as follows:

1) extracting the preparation of the traditional Chinese medicine composition using a nonpolar solvent to obtain a test solution;
2) preparing a solution of menthol reference substance with a menthol concentration of 4.80 μg/mL or more by a menthol reference substance using the same non-polar solvent as that in step 1);
3) taking the solution of menthol reference substance and the test solution in an equal amount respectively, injecting the solutions into a gas chromatograph, and determining the contents of menthol, wherein the conditions for chromatography are:
the column is a capillary chromatographic column containing phenyl-methyl polysiloxane as a stationary phase, the phenyl-methyl polysiloxane has a phenyl content of 1-10% and is a chromatographic column of type HP-5 or type DB-5; the column temperature is increased according to the following temperature programming: initial temperature is 80-100° C., and is kept for 10-15 minutes, increased to 120-160° C. at a rate of 6-10° C. per minute, kept for 1.5-3.5 minutes, then increased to 240-300° C. at a rate of 100-160° C. per minute, kept for 5-20 minutes.

2. The method according to claim 1, wherein the mass-to-volume ratio of the preparation of the traditional Chinese medicine composition to the non-polar solvent as used is (1 g: 400 mL) to (1 g: 50 mL) during the preparation of the test solution.

3. The method according to claim 1, wherein the phenyl-methyl polysiloxane has a phenyl content of 5%.

4. The method according to claim 1, wherein the solution of menthol reference substance and the test solution are injected in an amount of 0.5-2 μL.

5. The method according to claim 1, wherein the solution of menthol reference substance and the test solution are injected by split injection with a split ratio in the range of 50:1 to 10:1 during determination of the menthol content.

6. The method according to claim 5, wherein the solution of menthol reference substance and the test solution are injected by split injection with a split ratio in the range of 30:1 to 20:1 during determination of the menthol content.

7. The method according to claim 5, wherein the solution of menthol reference substance and the test solution are injected by split injection with a split ratio in the range of 25:1 during determination of the menthol content.

8. The method according claim 1, wherein the conditions for chromatography also comprise detector temperature and inlet temperature of 300-400° C.

9. The method according to claim 1, wherein the conditions for chromatography also comprise carried gas and flow rate thereof, the carrier gas is nitrogen with a flow rate of 0.8-1.2 mL/min.

10. The method according to claim 1, wherein the conditions for chromatography also comprises a fuel gas ratio, the fuel gas ratio is the ratio of air to hydrogen being from 8:1 to 12:1.

11. The method according to claim 10, wherein the fuel gas ratio is the ratio of air to hydrogen being 9:1 to 11:1.

12. The method according to claim 10, wherein the fuel gas ratio is the ratio of air to hydrogen being 10:1.

13. The method according to claim 1, wherein the non-polar solvent is selected from the group consisting of non-polar saturated alkanes or halogenated saturated alkanes, and non-polar ester solvents.

14. The method according to claim 13, wherein the non-polar solvent is selected from the group consisting of n-hexane, dichloromethane, petroleum ether and ethyl acetate.

15. The method according to claim 1, wherein the method for preparing the test solution specifically is as follows: grinding and mixing the preparation of the traditional Chinese medicine composition evenly, placing the obtained substance in a narrow mouth container equipped with a plug, adding the non-polar organic solvent, shaking for 20 seconds or more, filtering then obtaining the test solution.

16. The method according to claim 15, wherein the filtering step is carried out using a 0.2-0.4 μm microporous filter.

17. The method according to claim 15, wherein the filtering step is carried out using a 0.22 μm microporous filter.

18. The method according to claim 15, wherein the method for preparing the test solution further comprises the step of soaking or ultrasonical extraction at room temperature before the shaking step.

19. The method according to claim 1, wherein 2) preparing a solution of menthol reference substance with a menthol concentration of 17.65 μg/mL or more by a menthol reference substance using the same non-polar solvent as that in step 1).

20. The method according to claim 1, wherein 2) preparing a solution of menthol reference substance with a menthol concentration of 0.2-0.3 mg/mL by a menthol reference substance using the same non-polar solvent as that in step 1).

* * * * *